United States Patent [19]

Drabek et al.

[11] 4,161,536

[45] Jul. 17, 1979

[54] PESTICIDAL ALIPHATIC CARBOXYLATES

[75] Inventors: Jozef Drabek, Oberwil; Saleem Farooq, Aesch; Laurenz Gsell, Füllinsdorf; Odd Kristiansen, Möhlin; Willy Meyer, Riehen, all of Switzerland

[73] Assignee: Ciba-Geigy Corporation, Ardsley, N.Y.

[21] Appl. No.: 849,150

[22] Filed: Nov. 7, 1977

[30] Foreign Application Priority Data

Nov. 12, 1976 [CH] Switzerland .................. 14284/76
Sep. 29, 1977 [CH] Switzerland .................. 11910/77

[51] Int. Cl.² .................. A01N 9/20; A01N 9/24; C07C 69/65; C07C 121/75
[52] U.S. Cl. .................. 424/304; 260/465 D; 260/544 Y; 560/219; 562/598; 424/314
[58] Field of Search .................. 260/465 D; 560/219; 424/304, 314

[56] References Cited

U.S. PATENT DOCUMENTS 3,996,244 12/1976 Fujimoto et al. ............. 260/332.2 A
4,042,710 8/1977 Bull et al. ............................. 424/304

Primary Examiner—Dolph H. Torrence
Attorney, Agent, or Firm—Frederick H. Rabin

[57] ABSTRACT

Aliphatic carboxylic acid esters of the formula

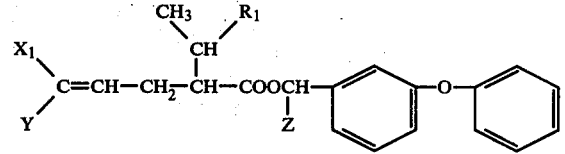

wherein
$R_1$ represents hydrogen or methyl,
$X_1$ represents halogen,
Y represents halogen or methyl, and
Z represents cyano or ethynyl, processes for producing them and their use in combating pests.

12 Claims, No Drawings

PESTICIDAL ALIPHATIC CARBOXYLATES

DETAILED DISCLOSURE

The present invention relates to aliphatic carboxylic acid esters, to processes for producing them and to their use in combating pests.

The aliphatic carboxylic acid esters have the formula

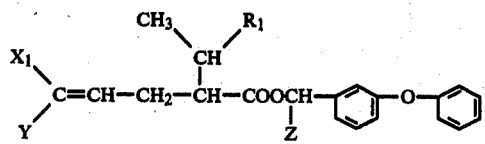

wherein
- $R_1$ represents hydrogen or methyl,
- $X_1$ represents halogen,
- Y represents halogen or methyl, and
- Z represents cyano or ethynyl.

By halogen in this case is meant fluorine, chlorine, bromine or iodine, but particularly chlorine. Compounds of the formula I preferred by virtue of their action are those wherein $R_1$ represents hydrogen or methyl, $X_1$ and Y each represent chlorine, and Z represents cyano.

The compounds of the formula I are produced by methods known per se, for example as follows:

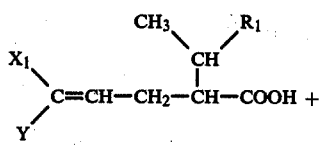

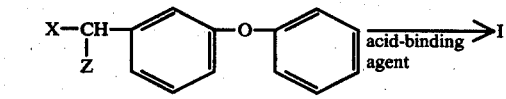

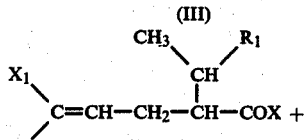

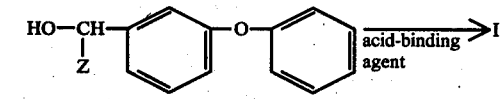

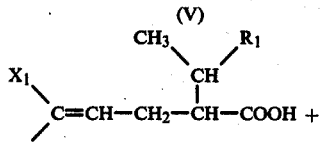

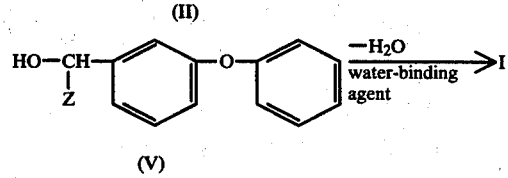

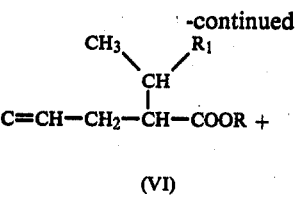

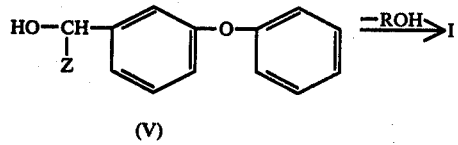

In the formulae II to VI, the symbols $R_1$, $X_1$, Y and Z have the meanings given under the formula I. In the formulae III and IV, X represents a halogen atom, particularly chlorine or bromine, and in the formula VI, R represents $C_1$-$C_4$-alkyl, especially methyl or ethyl. Suitable acid-binding agents for the processes 1 and 2 are, in particular, tertiary amines, such as trialkylamines and pyridine, also hydroxides, oxides, carbonates and bicarbonates of alkali metals and alkaline-earth metals, and also alkali metal alcoholates such as potassium-t.-butylate and sodium methylate. The water-binding agent used for the process 3 can be, for example, dicyclohexylcarbodiimide. The processes 1 to 4 are performed at a reaction temperature of between $-10°$ and $+100°$ C., generally between 20 and 80° C., at normal or elevated pressure and preferably in an inert solvent or diluent. Suitable solvents or diluents are, for example, ethers and ethereal compounds such as diethyl ether, dipropyl ether, dioxane, dimethoxyethane and tetrahydrofuran; amides such as N,N-dialkylated carboxylic acid amides; aliphatic aromatic and also halogenated hydrocarbons, particularly benzene, toluene, xylene, chloroform and chlorobenzene; nitriles such as acetonitrile; dimethylsulphoxide and ketones such as acetone and methyl ethyl ketone. The process 2 can be performed also in an aqueous medium.

The starting materials of the formulae II to VI are known or can be produced by methods analogous to known methods. One method of producing the compound of the formula II is described in Example I.

Unless homogeneous optically active starting materials are used in the production process, the compounds of the formula I are obtained as mixtures of various optically active isomers. The different isomeric mixtures can be separated by known methods into the individual isomers. By 'compound of the formula I' is meant both the individual isomers and mixtures thereof.

The compounds of the formula I are suitable for combating various animal and plant pests. They are suitable in particular for combating insects and phytopathogenic mites and ticks, e.g. of the orders Lepidoptera, Coleoptera, Homoptera, Heteroptera, Diptera, Acarina, Thysanoptera, Orthoptera, Anoplura, Siphonoptera, Mallophaga, Thysanura, Isoptera, Psocoptera and Hymenoptera.

Compounds of the formula I are especially suitable for combating insects which damage plants, particularly insects which damage plants by eating, in crops of ornamental plants and useful plants, especially in cotton crops, (e.g. against *Spodoptera littoralis* and *Heliothis virescens*) and in crops of vegetables (e.g. against *Leptinotarsa decemlineata* and *Myzus persicae*). The active substances of the formula I also exhibit a very favourable action against flies, such as *Musca domestica*, and against mosquito larvae.

The acaricidal and insecticidal action can be substantially broadened and adapted to suit given circumstances by the addition of other insecticides and/or acaricides. Suitable additives are, for example, organic phosphorus compounds, nitrophenols and derivatives thereof, formamidines, ureas, other pyrethrin-like compounds, and also carbamates and chlorinated hydrocarbons.

Compounds of the formula I are combined particularly advantageously also with substances which have a synergistic or intensifying effect on pyrethroids. Examples of such compounds are, inter alia, piperonylbutoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-(octylsulphonyl)-propyl)-benzene.

Compounds of the formula I can be used on their own or together with suitable carriers and/or additives. Suitable additives can be solid or liquid and they correspond to the substances common in formulation practice, such as natural or regenerated substances, solvents, dispersing agents, wetting agents, adhesives, thickeners, binders and/or fertilisers.

The compositions according to the invention are produced in a manner known per se by the intimate mixing and/or grinding of the active substances of the formula I with suitable carriers, optionally with the addition of dispersing agents or solvents which are insert to the active substances. The active substances can be obtained and used in the following forms:

solid preparations: dusts, scattering agents, granules, (coated granules, impregnated granules and homogeneous granules);

liquid preparations:
(a) water-dispersible concentrates of active substance: wettable powders, pastes or emulsions;
(b) solutions.

The content of active substance in the compositions described is between 0.1 and 95%; it is to be mentioned in this respect that with application from an aeroplane, or by other suitable devices, concentrations of up to 99.5% or even the pure active substance can be used.

The active substances of the formula I can be formulated for example as follows (parts are by weight):

Dusts

The following substances are used to produce (a) a 5% dust and (b) a 2% dust:

(a)
5 parts of active substance,
95 parts of talcum;

(b)
2 parts of active substance,
1 part of highly dispersed silicic acid,
97 parts of talcum.

The active substance is mixed and ground with the carriers.

Granulate

The following ingredients are used to produce a 5% granulate:

5 parts of active substance,
0.25 part of epichlorohydrin,
0.25 part of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The solution obtained is sprayed onto kaolin and the acetone is evaporated off in vacuo.

Wettable Powder

The following constituents are used to produce (a) a 40%, (b) and (c) a 25%, and (d) a 10% wettable powder:

(a)
40 parts of active substance,
5 parts of sodium lignin sulphonate,
1 part of sodium dibutyl-naphthalene sulphonate,
54 parts of silicic acid;

(b)
25 parts of active substance,
4.5 parts of calcium lignin sulphonate,
1.9 parts of Champagne chalk/hydroxyethyl cellulose mixture (1:1),
1.5 parts of sodium dibutyl-naphthalene sulphonate,
19.5 parts of silicic acid,
19.5 parts of Champagne chalk,
28.1 parts of kaolin;

(c)
25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;

(d)
10 parts of active substance,
3 parts of a mixture of the sodium salts of saturated fatty alcohol sulphates,
5 parts of naphthalenesulphonic acid/formaldehyde condensate,
82 parts of kaolin.

The active substance is intimately mixed in suitable mixers with the additives, and the mixture is then ground in the appropriate mills and rollers to obtain wettable powders which can be diluted with water to give suspensions of the desired concentration.

Emulsifiable Concentrates

The following substances are used to produce (a) a 10%, (b) a 25% and (c) a 50% emulsifiable concentrate:

(a)
10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

(b)
25 parts of active substance,
2.5 parts of epoxidised vegetable oil,
10 parts of an alkylarylsulphonate/fatty alcohol polyglycol ether mixture,
5 parts of dimethylformamide,
57.5 parts of xylene;

(c)
50 parts of active substance,
4.2 parts of tributylphenol-polyglycol ether,
5.8 parts of calcium-dodecylbenzenesulphonate, 20 parts of cyclohexanone,
20 parts of xylene.

Emulsions of the concentration required can be prepared from these concentrates by dilution with water.

Spray

The following constituents are used to produce (a) a 5% spray and (b) a 95% spray:

(a)
5 parts of active substance,
1 part of epichlorohydrin,
94 parts of ligroin (boiling limites 160°–190° C.);

(b)
95 parts of active substance,
5 parts of epichlorohydrin.

The invention is further illustrated by the following Examples.

EXAMPLE 1

Production of 2-isopropyl-5-chlorohexene(3)-carboxylic acid α-cyano-m-phenoxy-benzyl ester 5.6 g of 2-isopropyl-5-chlorohexene(3)-carboxylic acid and 2.4 ml of thionyl chloride in 30 ml of hexane are refluxed for four hours. After the hexane has been removed by distillation, the acid chloride remaining behind is added dropwise at 0 to 5° C. to a solution of 6.6 g of α-cyano-m-phenoxybenzyl alcohol, 3 ml of pyridine and 25 ml of benzene. The mixture is stirred for one hour and then allowed to stand for 12 hours; it is subsequently poured into ice water and extracted with ether. The ether solution is washed with 3% hydrochloric acid solution, 3% sodium bicarbonate solution and with water; and then dried over sodium sulphate. After removal of the ether by distillation and chromatographic purification of the crude product (silica gel; eluent hexane/ether 5:1), there is obtained the compound of the formula

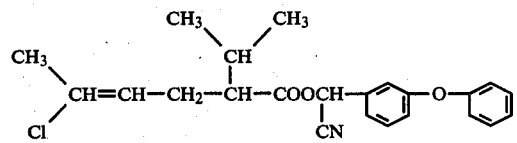

in the form of light-yellow oil having a refractive index of $n_D^{20}$: 1.5380.

The following compounds are produced in an analogous manner:

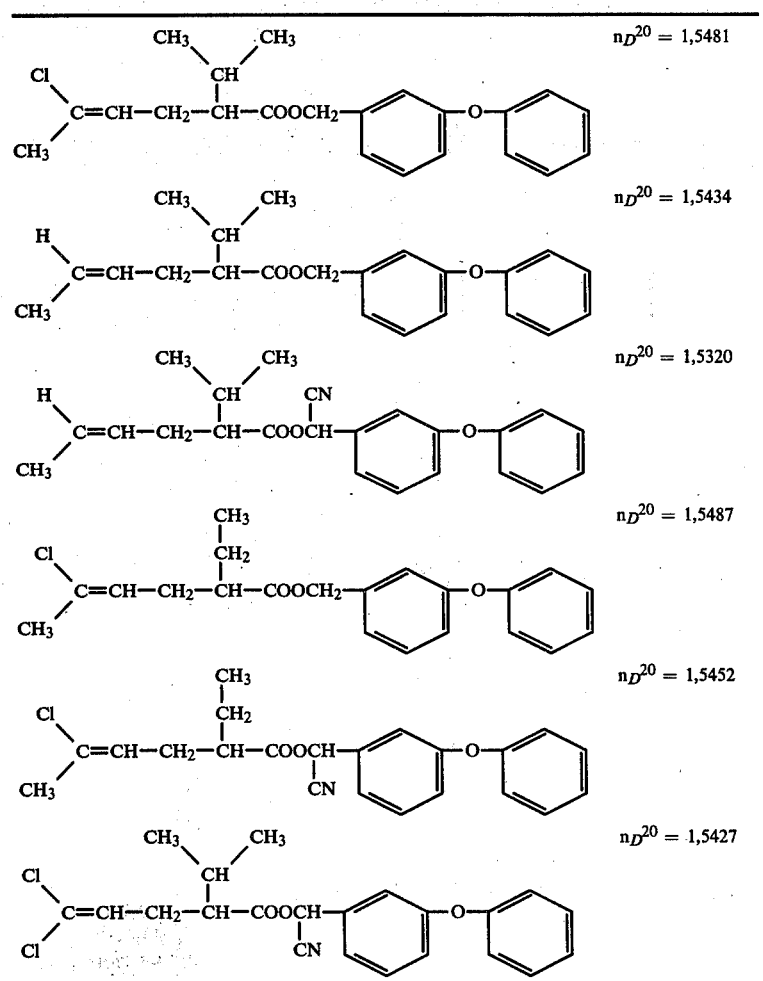

-continued

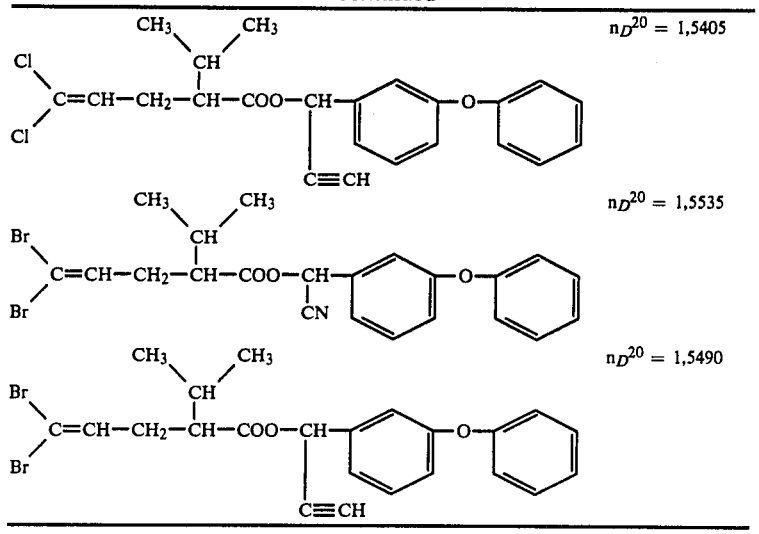

EXAMPLE 2

(A) Insecticidal stomach-poison action

Tobacco and potato plants were sprayed with a 0.05% aqueous active-substance emulsion (obtained from a 10% emulsifiable concentrate).

After drying of the coating, caterpillars of *Spodoptera littoralis* in the $L_3$-stage and of *Heliothis virescens* in the $L_3$-stage were placed onto the tobacco and potato plants. The test was carried out at 24° C. with 60% relative humidity.

The compounds according to Example 1 exhibited in the above test a good insecticidal stomach poison action against *Spodoptera littoralis* and *Heliothis virescens* caterpillars.

(B) Insecticidal contact action

One day before application of the active-substance emulsion, broad beans (*Vicia faba*) grown in pots were infested with about 200 bean aphids (*Aphis fabae*) per plant. The spray emulsion at a concentration of 1000 ppm (prepared from a 25% wettable powder) was applied by means of a compressed-air sprayer to the leaves infested with aphids. An evaluation was made 24 hours after application. The compounds according to Example 1 exhibited in the above test a good contact action against *Aphis fabae*.

We claim:

1. An aliphatic carboxylic acid ester of the formula

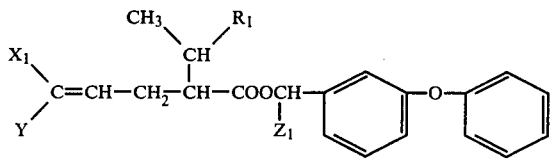

wherein
$R_1$ represents hydrogen or methyl,
$X_1$ represents halogen,
Y represents halogen or methyl, and
Z represents cyano or ethynyl.

2. An aliphatic carboxylic acid ester according to claim 1, wherein $X_1$ and Y each represent chlorine, and Z represents cyano.

3. The aliphatic carboxylic acid ester according to claim 1, which corresponds to the formula

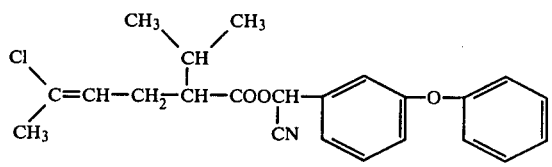

4. The aliphatic carboxylic acid ester according to claim 1, which corresponds to the formula

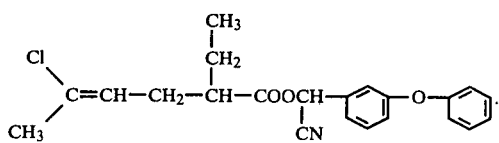

5. The aliphatic carboxylic acid ester according to claim 2, which corresponds to the formula

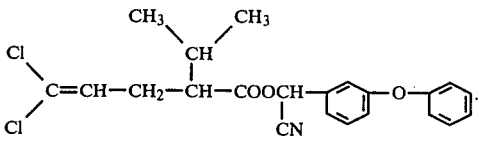

6. The aliphatic carboxylic acid ester according to claim 2, which corresponds to the formula

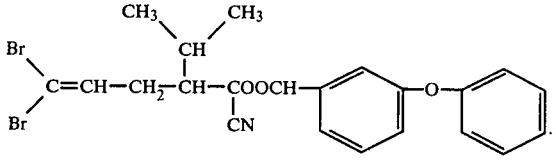

7. A pesticidal composition which comprises a compound according to claim 1 as active ingredient, and suitable carriers and/or other additives.

8. A method for combatting insects which comprises applying thereto an insecticidally effective amount of a compound of the formula

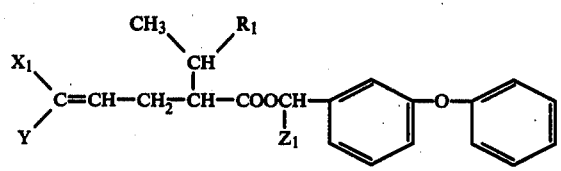

wherein
R₁ represents hydrogen or methyl,
X₁ represents halogen,
Y represents halogen or methyl, and
Z represents cyano or ethynyl.

9. The method according to claim 8 in which the compound is

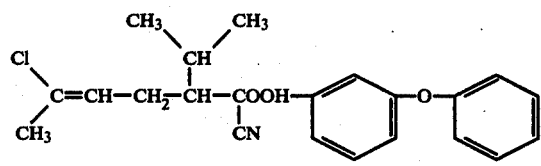

10. The method according to claim 8 in which the compound is

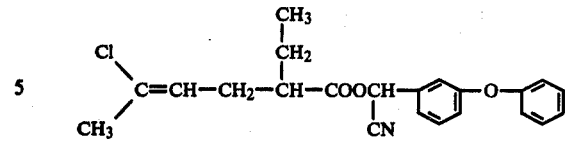

11. The method according to claim 8 in which the compound is

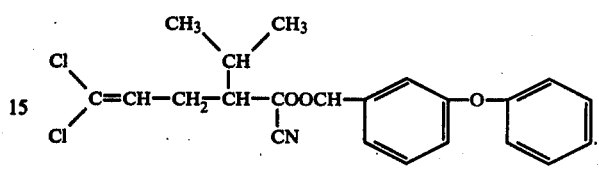

12. The method according to claim 8 in which the compound is

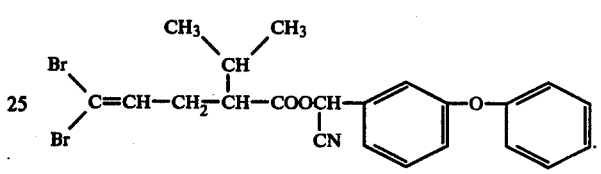

* * * * *